United States Patent [19]
Smith et al.

[11] Patent Number: 5,824,046
[45] Date of Patent: Oct. 20, 1998

[54] COVERED STENT

[75] Inventors: Scott R. Smith, Chaska; David Sogard, Edina; Susan Shoemaker, Elk River, all of Minn.

[73] Assignee: Scimed Life Systems, Inc., Maple Grove, Minn.

[21] Appl. No.: 720,091

[22] Filed: Sep. 27, 1996

[51] Int. Cl.$^6$ .................................. A61F 2/06; A61F 2/04
[52] U.S. Cl. .................................................. 623/1; 600/36
[58] Field of Search .................... 623/1, 11, 12; 600/36

[56] References Cited

U.S. PATENT DOCUMENTS

| | | |
|---|---|---|
| 3,657,744 | 4/1972 | Ersek . |
| 4,300,244 | 11/1981 | Bokros . |
| 4,385,093 | 5/1983 | Hubis .................................. 428/316.6 |
| 4,409,172 | 10/1983 | Ward, Jr. et al. . |
| 4,478,665 | 10/1984 | Hubis ...................................... 156/229 |
| 4,482,516 | 11/1984 | Bowman et al. ........................ 264/127 |
| 4,503,569 | 3/1985 | Dotter . |
| 4,580,568 | 4/1986 | Gianturco . |
| 4,598,011 | 7/1986 | Bowman .................................. 428/221 |
| 4,604,762 | 8/1986 | Robinson . |
| 4,731,073 | 3/1988 | Robinson . |
| 4,732,152 | 3/1988 | Wallsten et al. . |
| 4,733,665 | 3/1988 | Palmaz . |
| 4,856,516 | 8/1989 | Hillstead . |
| 4,886,062 | 12/1989 | Wiktor . |
| 4,955,899 | 9/1990 | Corna et al. ................................. 623/1 |
| 5,078,726 | 1/1992 | Kreamer . |
| 5,123,917 | 6/1992 | Lee . |
| 5,175,052 | 12/1992 | Tokuda et al. . |
| 5,192,310 | 3/1993 | Herweck et al. ............................ 623/1 |
| 5,197,978 | 3/1993 | Hess .............................................. 623/1 |
| 5,282,824 | 2/1994 | Gianturco . |
| 5,330,500 | 7/1994 | Song . |
| 5,366,504 | 11/1994 | Andersen et al. . |
| 5,383,926 | 1/1995 | Lock et al. . |
| 5,389,106 | 2/1995 | Tower . |
| 5,474,727 | 12/1995 | Perez . |
| 5,522,881 | 6/1996 | Lentz . |
| 5,522,882 | 6/1996 | Gaterud et al. .............................. 623/1 |
| 5,628,782 | 5/1997 | Myers et al. ................................. 623/1 |
| 5,674,241 | 10/1997 | Bley et al. ................................... 623/1 |
| 5,681,345 | 10/1997 | Euteneuer .................................... 623/1 |
| 5,693,085 | 12/1997 | Buirge et al. ............................... 623/1 |

FOREIGN PATENT DOCUMENTS

| | | |
|---|---|---|
| 0 539 237 | 4/1993 | European Pat. Off. . |
| 0 657 147 | 6/1995 | European Pat. Off. . |
| 0657147 | 6/1995 | European Pat. Off. .................. 623/1 |
| 1457 921 | 2/1989 | U.S.S.R. . |
| WO 96/35577 | 11/1986 | WIPO . |
| WO 95/05132 | 2/1995 | WIPO . |
| WO 95/29647 | 11/1995 | WIPO . |
| WO 96/00103 | 1/1996 | WIPO . |
| WO 96/03092 | 2/1996 | WIPO . |
| WO 96/10967 | 4/1996 | WIPO . |
| WO 96/22745 | 8/1996 | WIPO . |
| WO 96/26689 | 9/1996 | WIPO . |
| WO 96/28115 | 9/1996 | WIPO . |

OTHER PUBLICATIONS

Percutaneous Endovascular Graft: Experimental Evaluation by David D. Lawrence, Jr., M.D., Chusilp Charnsangavej, M.D., Kenneth C. Wright, Ph.D., Cesar Gianturco, M.D. Sidney Wallace, M.D., Radiology, May 1987, pp. 357–360.

Primary Examiner—Michael J. Milano
Assistant Examiner—Tram Anh T. Nguyen
Attorney, Agent, or Firm—Hoffmann & Baron, LLP

[57] ABSTRACT

A composite intraluminal device is deployable within a body vessel. The composite device includes an elongate radially expandable tubular stent having an interior luminal surface and an opposed exterior surface extending along a longitudinal stent axis. A stent cover is formed of unsintered ePTFE which is expandable. The stent cover is positioned about the stent so as to permit expansion of the cover upon the radial expansion of the stent.

14 Claims, 7 Drawing Sheets

COVERED STENT

FIELD OF THE INVENTION

The present invention relates generally to an implantable intraluminal device. More particularly, the present invention relates to a composite intraluminal device including a stent and stent cover.

BACKGROUND OF THE INVENTION

It is well known to employ various endoprostheses for the treatment of diseases of various body vessels. One type of endoprosthesis is commonly referred to as a stent. A stent is a generally longitudinal tubular device formed of biocompatible material which is useful in the treatment of stenosis, strictures or aneurysms in body vessels such as blood vessels. These devices are implanted within the vessel to reinforce collapsing, partially occluded, weakened or abnormally dilated sections of the vessel. Stents are typically employed after angioplasty of a blood vessel to prevent restenosis of the diseased vessel. While stents are most notably used in blood vessels, stents may also be implanted in other body vessels such as the urogenital tract and bile duct.

Stents generally include an open flexible configuration. This configuration allows the stent to be inserted through curved vessels. Furthermore, the stent configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Examples of various stent constructions are shown in U.S. Pat. Nos. 4,503,569 to Dotter; 4,733,665 to Palmaz; 4,856,561 to Hillstead; 4,580,568 to Gianturco; 4,732,152 to Wallsten and 4,886,062 to Wiktor, each of which are incorporated by reference herein. Additionally, published PCT WO96/26689 entitled "Improved Longitudinally Flexible Expandable Stent", and its priority U.S. applications 08/396,569 filed Mar. 1, 1995 and 08/511,076 filed Aug. 3, 1995 are also incorporated by reference herein.

While the stents of such construction perform adequately for the purpose of holding open otherwise blocked, weakened or occluded vessels, due to the open nature of the stent there is a tendency for the stent to permit passage of material through the body of the stent. Such material may include excessive cell or tissue growth (intimal hyperplasia), thrombus formations and plaque in vascular situations and tumors in the bile or urogenital tract. These materials may have a tendency to block or otherwise re-occlude the open vessel.

One technique to reduce the susceptibility for materials to pass through the wall of the deployed stent includes providing a composite intraluminal device including a stent and an outer covering which would surround the open stent construction. While such covers would prevent material from passing through the stent wall, the covering itself must be sufficiently flexible and expandable so as to permit deployment of the stent from its compressed condition to its radially expanded condition.

Examples of composite intraluminal devices are described in the following U.S. patents.

U.S. Pat. No. 5,123,916 to Lee describes in expandable intraluminal vascular graft which includes concentric cylindrical tubes having a plurality of scaffold members mounted there between. The scaffold members are expandable, ring-like and provide circumferential rigidity to the graft.

U.S. Pat. No. 5,383,926 to Lock, et al. describes a radially expandable endoprosthesis which comprises an elongated sleeve member in which the radially outward expansion of the sleeve is limited by connecting strips. These strips are selectively removable to allow further outward expansion. The sleeve can be C-shaped in cross-section to allow for further expanded growth. The sleeve member generally has an open wall structure such as those typical of wire mesh tubing or slotted tubing. An expandable sheet material may be disposed across the open region of the C-shaped sleeve member and may be formed of Goritex®.

U.S. Pat. No. 5,389,106 to Tower discloses an impermeable expandable intravascular stent. An impermeable deformable membrane interconnects portions of a distensible frame to form an impermeable exterior wall to the frame. The membrane is formed of a synthetic non-latex, non-vinyl polymer and the frame is made from a fine wire of annealed platinum. The distensible frame may be an expandable stent and the membrane is a hypoallergenic biologically inert material that is free of latex rubber proteins. The membrane should be impermeable and have the properties of elasticity, distensibility and barrier protection. No specific classes of materials are mentioned except the product name Tactylon®. The impermeable membrane is attached to the stent by dipping the stent into the polymer solution of the membrane and subsequently drying the device to remove the solvent. The stent is imbedded within the membrane surface.

Another type of covered stent which permits radial expansion is shown in WO 96/00103 having an international publication date of Jan. 4, 1996. As shown and described therein, a metallic expandable stent includes an outer covering of ePTFE. The ePTFE cover exhibits suitable expansion capabilities so as to enable the cover to expand upon expansion of the underlying stent. However, in order to impart the expandable characteristics to the ePTFE cover, during formation the ePTFE material forming the cover must undergo the successive processing steps of expanding the material, sintering the material, radially dilating the material and resintering the dilated material. The ePTFE cover so formed is sufficiently expandable so as to enable the cover to exhibit the required expansion characteristics. However the device described above requires precise manufacturing techniques and is extremely processing sensitive. Careful processing of the material forming the cover is required in order for the cover to exhibit sufficient expansion capabilities. It is therefore desirable to provide a covered stent where the cover is radially expandable with the stent and where the cover may be easily manufactured and applied to the stent.

SUMMARY OF THE INVENTION

It is an object of the present invention to provide an intraluminal prosthetic device such as a stent which will hold open an occluded, weakened or damaged vessel.

It is a further object of the present invention to provide a covered stent for intraluminal use which is designed to hold open a damaged lumen and to prevent material passage through the body of the stent.

It is a still further object of the present invention to provide an expandable covered stent which may be deployed intraluminally wherein the cover of the stent expands with the expansion of the stent.

In the efficient attainment of these and other objects, the present invention provides a composite intraluminal device including an elongate radially expandable tubular stent having an interior luminal surface and an opposed exterior surface extending along a longitudinal stent axis. A stent cover is formed of unsintered ePTFE which is expandable and which is positioned about the stent for expansion with the radial expansion of the stent.

In one preferred embodiment, the stent cover includes a longitudinal segment of unsintered ePTFE generally aligned longitudinally along the longitudinal stent axis. The longitudinal segment is expandable in a transverse direction upon radial expansion of the stent.

In a further embodiment of the invention, the stent cover includes an elongate segment of unsintered ePTFE having an original longitudinal expanse. The segment is expanded in a transverse direction so as to reduce the original longitudinal expanse. The cover is positioned generally transverse to the longitudinal stent axis. The expanded segment is expandable longitudinally upon radial expansion of the stent to return the expanded segment to the original longitudinal expanse to control the radial expansion of the stent. Further in this embodiment, the cover may be positioned with respect to the stent in a manner where the longitudinal stent axis lays orthogonally (i.e. at an acute off axis angle) with respect to the cover.

In a method aspect, the present invention provides a method of forming an intraluminal device. The method includes the step of providing an elongate radially expandable tubular stent. An elongate stent cover is formed of unsintered ePTFE. The stent cover is expandable in a transverse direction. The stent cover is applied about the stent with the stent cover longitudinally aligned with the stent so as to prevent transverse expansion of the cover upon radial expansion of the stent.

DETAILED DESCRIPTION OF THE PREFERRED EMBODIMENTS

The present invention provides a composite covered stent which may be implanted intraluminally within a body vessel and disposed adjacent an occluded, weakened or otherwise damaged portion of the vessel so as to hold the vessel open. The covered stent is typically delivered intraluminally via a balloon catheter. The device is delivered in a compressed condition and once properly positioned may be deployed by radial expansion. The most common form of deploying the intraluminal device is by balloon expansion, however, the present invention may also be deployed by use of a self-expanding stent.

Figure 1:
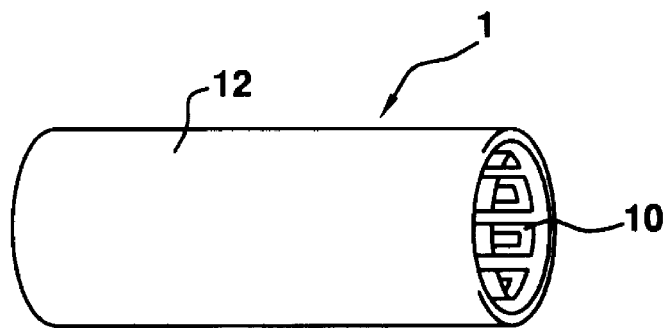
FIG. 1 is a perspective showing of the composite intraluminal device of the present invention.
Figure 3:
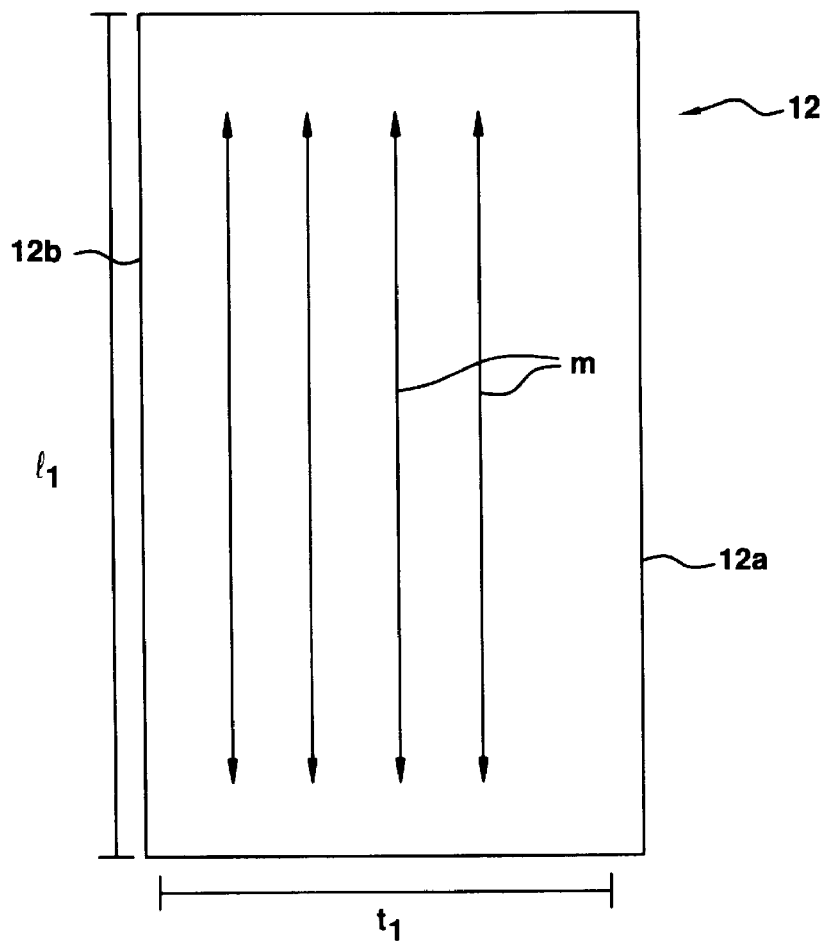
FIG. 3 is a perspective showing of a stent cover employed in the composite device shown in FIG. 1.

The composite intraluminal device 1 of the present invention takes the form of a stent 10 which may be of the type shown in FIG. 1 and a liner or cover 12 which may be of the type shown in FIG. 3. In use in a preferred arrangement the cover 12 is disposed over stent 10.

Figure 2:
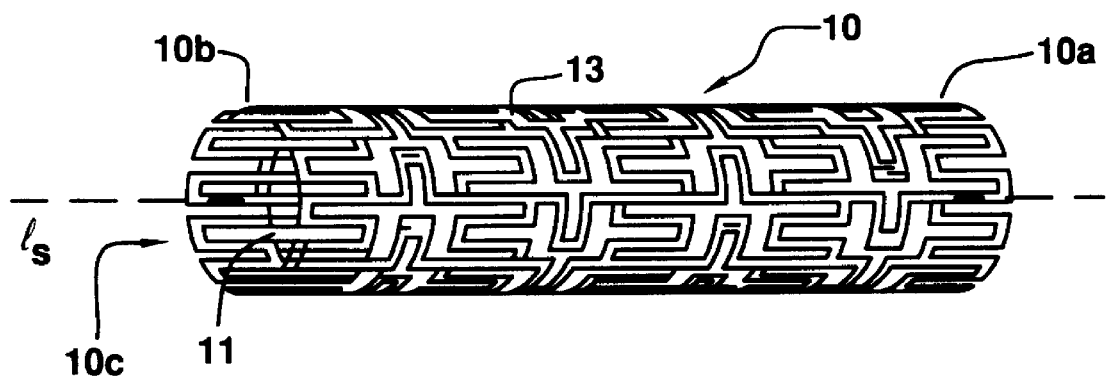
FIG. 2 is a perspective showing of a stent of the type which may be used in the composite device shown in FIG. 1.

Referring specifically to FIG. 2, stent 10 is generally an elongate tube having a longitudinal stent axis $l_s$. Stent 10 has opposed open ends 10a and 10b and a central lumen 10c therebetween. The body of stent 10 defines an opposed interior surface 11 and exterior surface 13 and is formed of a generally open configuration having a plurality of openings or passages through the body. These openings or passages provide for longitudinal flexibility of the stent as well as permitting the stent to be radially expanded once deployed in the body lumen.

The stent of the present invention is of the type more fully shown and described in International Patent Application No. WO 96/03092A1 published on Feb. 8, 1996, which along with its priority U.S. patent applications Ser. No. 282,181 filed Jul. 28, 1994 and Ser. No. 457,354 filed May 31, 1995, are incorporated by reference herein. The stent shown therein has a patterned shape having first and second meandering patterns extending orthogonally to each other. The particular meandering pattern and the opening or spaces therebetween allows the stent to be easily deployed through curved blood vessels as it renders the stent longitudinally flexible. Furthermore, the particular configuration of the stent 10 disclosed herein allows the stent to be radially expanded without significant reduction in longitudinal expanse.

While the present invention discloses a particular construction of stent 10, any open stent configuration well known in the prior art may be employed. For example, wire stents having bodies formed of helically coiled wire with spaces defined between the helixes may be employed in combination with the present invention. Furthermore, stents formed of tubes having etched or patterned slots therethrough may also be employed. Such stents are well known in the art and are described in the above-incorporated U.S. patents.

Stent 10 may be employed in combination with liner or cover 12 shown in FIG. 3. Cover 12 may be applied, in a preferred embodiment, over tubular stent 10 so as to fully circumferentially surround stent 10. While the preferred embodiment contemplates employing cover 12 about the exterior surface 13 of stent 10 as shown in FIG. 1, it is also contemplated that cover 12 in the form of a liner may be placed about the interior surface 11 of stent 10. The cover 12 thereby forms an effective barrier about stent 10 preventing excessive cell or tissue ingrowth or thrombus formation through the expanded wall of tubular stent 10. However, in order for cover 12 to function effectively in combination with stent 10, cover 12 must exhibit sufficient expansion capabilities so as to enable the cover 12 to expand along with the radial expansion of stent 10.

The present invention contemplates use of a polymer material for cover 12 which exhibits sufficient expansion capabilities once positioned about stent 10. Such materials include extrudable, biocompatible polymers which exhibit or can be formed with a high degree of molecular orientation in one direction, i.e. material which is highly uniaxially oriented. These polymers exhibit the ability to expand in a direction substantially transverse to the direction of the uniaxial orientation. In the manufacture of polymer sheets, films and the like, typically the direction of orientation is the direction in which the material is formed. This is referred to as the machine direction (arrows M, FIG. 3). As the formation of the cover is typically accomplished by an extrusion process, the material is extruded along a longitudinal axis defining the machine direction. Material having uniaxial orientation in the machine direction would exhibit expansion in a direction substantially perpendicular thereto.

Figure 3A:
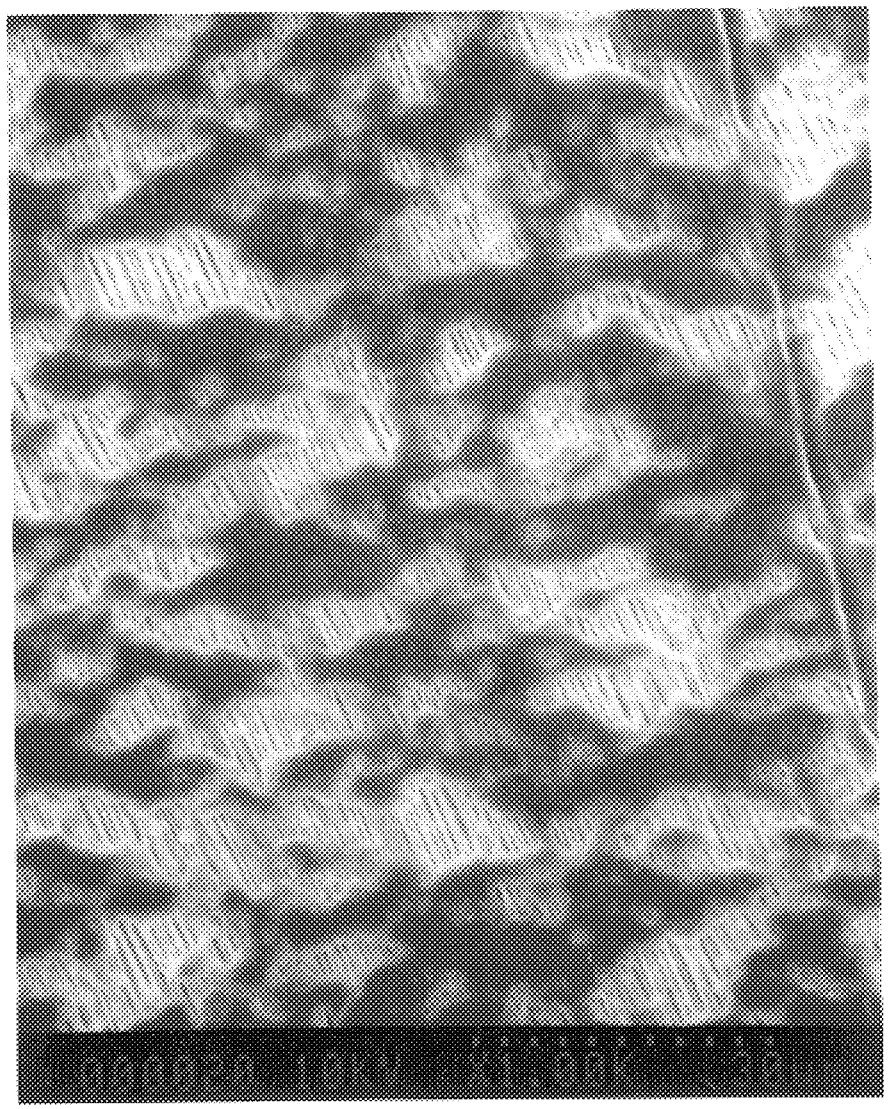
FIG. 3A is a photomicrograph of uniaxially oriented ePTFE material of the type forming the cover of FIG. 3.

In a preferred embodiment of the present invention, cover 12 may be formed from uniaxially oriented expanded polytetrafluoroethylene (ePTFE). As is well known in the art ePTFE films or sheets may be formed in a paste extrusion process. Paste extrusion yields a PTFE product in a "green" state. Once the lubricant is removed, such a material is highly friable, that is, the material is subjected to crumbling if handled and would not be useful in certain applications requiring structural strength. However, the green material being highly uniaxially oriented (along the machine direction), may be expanded or stretched in a direction transverse to the machine direction. Normally to expand PTFE, the material is heated and expanded longitudinally to yield ePTFE. The resulting material is more stable and less friable and may be more easily handled. This is due to the node and fibril structure resulting from longitudinal expansion. This structure is shown in FIG. 3A. However, once sintered, such ePTFE material does not exhibit the ability to be further expanded or stretched. The present invention employs unsintered ePTFE, which has been processed by heating, only to the extent necessary to yield a stable non-friable material. PTFE generally requires sintering at its melting point, i.e. about 327° C. to attain structural properties. The present covers are heated to a temperature insufficient to sinter the product, i.e. generally below about 327° C. If temperatures are used at or beyond the normal sintering range, it must be for a time insufficient to effectuate sintering. Once heat conditioned in this manner, this material still exhibits the ability to be stretched or expanded in a transverse direction and exhibits sufficient radial strength for purposes of the present invention.

Thus, as shown in FIG. 3, ePTFE cover 12 having been extruded in its longitudinal direction along longitudinal expanse $l_1$ would exhibit enhanced expansion capabilities along its transverse expanse $t_1$.

It has been found that certain commercially available PTFE materials exhibiting such properties may be employed in combination with the present invention. For instance, polytetrafluoroethylene tape may be used in combination with the present invention. The manufacture of such a tape is shown and described in U.S. Pat. No. 5,474,727 to Perez and U.S. Pat. No. 5,175,052 to Tokuda, each of which is incorporated by reference herein. The tape manufactured by the process described in the above-incorporated patents results in porous tape having little or no expansion capabilities in the longitudinal direction but exhibiting superior expansion capabilities in a direction substantially transverse thereto.

Figure 4:
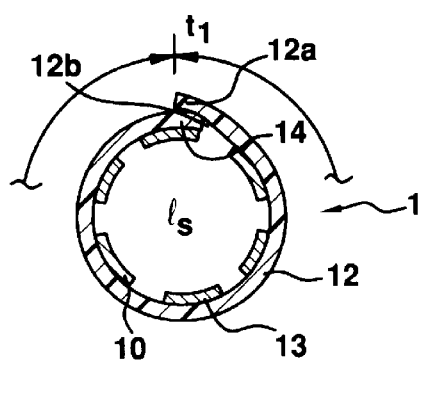
FIG. 4 is a cross-sectional view of one embodiment of the covered stent of the present invention shown in the compressed condition.
Figure 5:
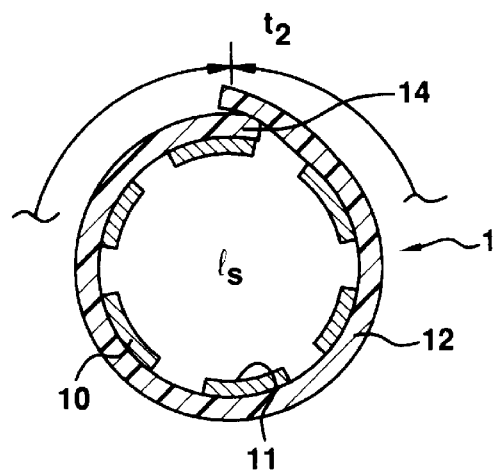
FIG. 5 is a cross-sectional view of the covered stent of FIG. 3 shown in the radially expanded condition.

In order to employ such ePTFE tape as a cover for a stent 10, a segment thereof forming cover 12 is provided. Referring to FIGS. 3–5, cover 12 is positioned so that its longitudinal expanse $l_1$ aligns with the longitudinal stent axis $l_s$ of stent 10. In preferred form, the cover 12 is wrapped around the exterior surface of stent 10 so that opposed longitudinal edges 12a and 12b overlie each other forming a seam 14. Edges 12a and 12b may be adhered to one another so as to provide a closed seam. Adhering techniques such a compression or adhesive bonding or anchoring may be employed to form closed seam 14. It is contemplated that weak electrostatic forces may be employed to bond together longitudinal edges 12a and 12b. No chemical bonding is necessary to form closed seam 14. Furthermore, an adhesive which will wet the material may also be applied so as to form an adhesive bond between the overlapped edges 12a and 12b. While cover 12 is shown attached to stent 10 by bonding overlapped edges 12a, 12b to form seam 14, it is further contemplated that cover 12 may be adhered to stent 10 at one or more locations therealong. Such securement is shown and described in commonly assigned U.S. patent application Ser. No. 08/721,834 filed at an even date herewith (as attorney docket no. 760-2) and entitled "Stent/Membrane Composite Device" which is incorporated by reference herein.

Once positioned about compressed stent 10, the ability of the material forming cover 12 to expand in a transverse direction allows the cover to be radially expanded upon the radial expansion of stent 10. Upon such radial stent expansion, either by balloon inflation or by self-expanding capabilities, cover 12 will expand transversely from a transverse dimension $t_1$ to a transverse dimension $t_2$ which is greater than $t_1$. As particularly shown in FIGS. 4 and 5, the transverse expanse $t_1$ of cover 12 forms the circumferential component of the cover 12 about the compressed stent 10. Upon the radial expansion of stent 10, the ability for the transverse component of cover 12 to expand from a dimension $t_1$ to a dimension $t_2$ allows this cover to expand radially with the expansion of stent 10. Thus, as shown in FIG. 5, cover 12 expands to a circumferential dimension of $t_2$ about expanded stent 10.

The ability of highly uniaxially oriented materials such as ePTFE to expand only in the direction transverse to the direction of extrusion (machine direction) allows the material to be used as a cover in a second embodiment of the present invention.

Figure 6:
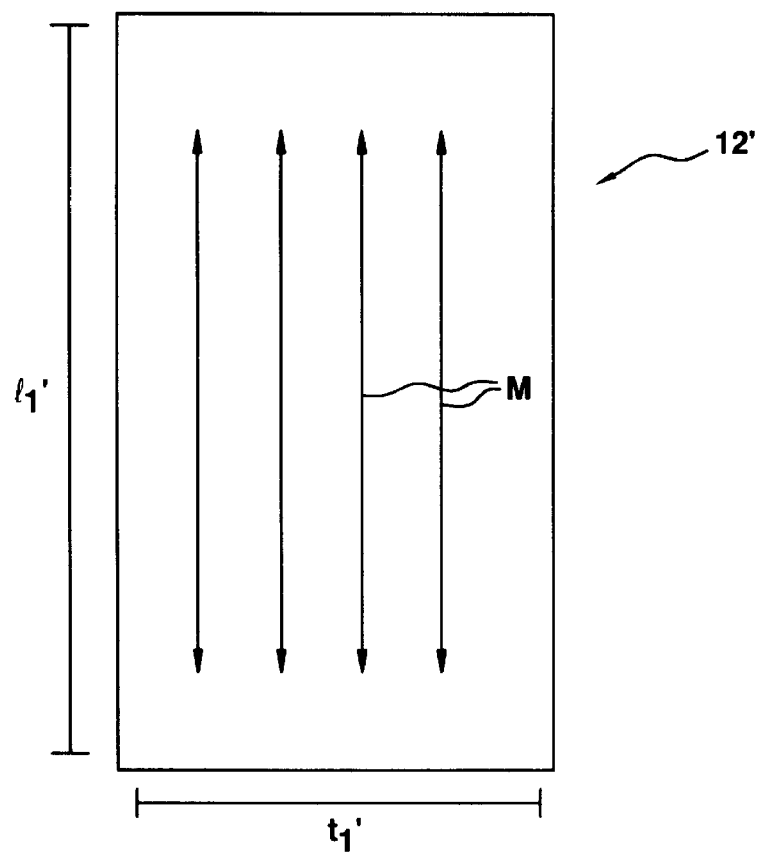
FIG. 6 is a perspective showing of a cover employed in a further embodiment of the present invention.
Figure 7:
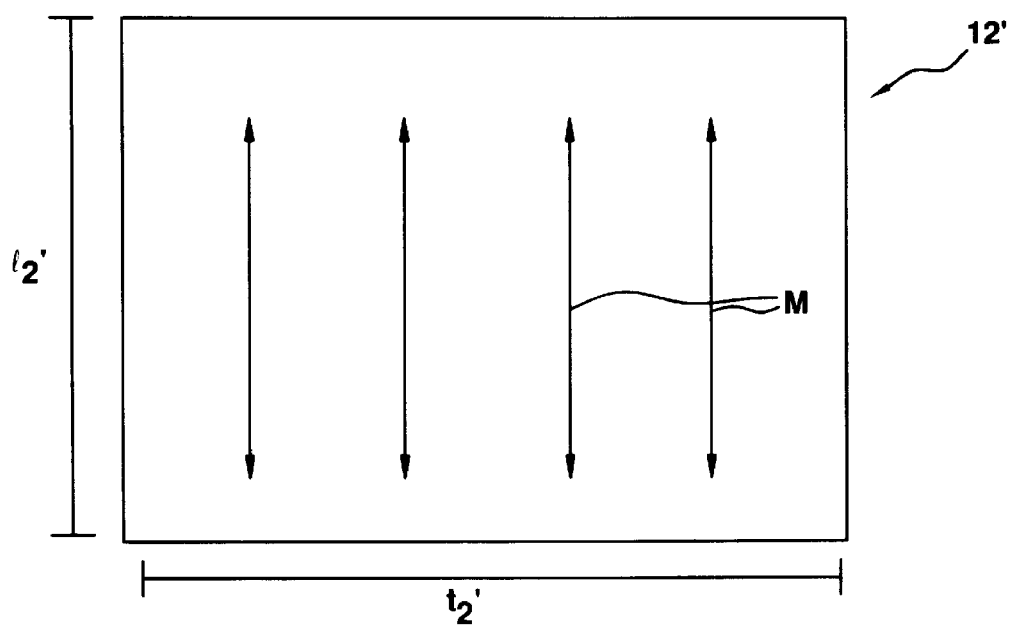
FIG. 7 shows the cover of FIG. 5 in a transversely expanded condition.
Figure 6A:
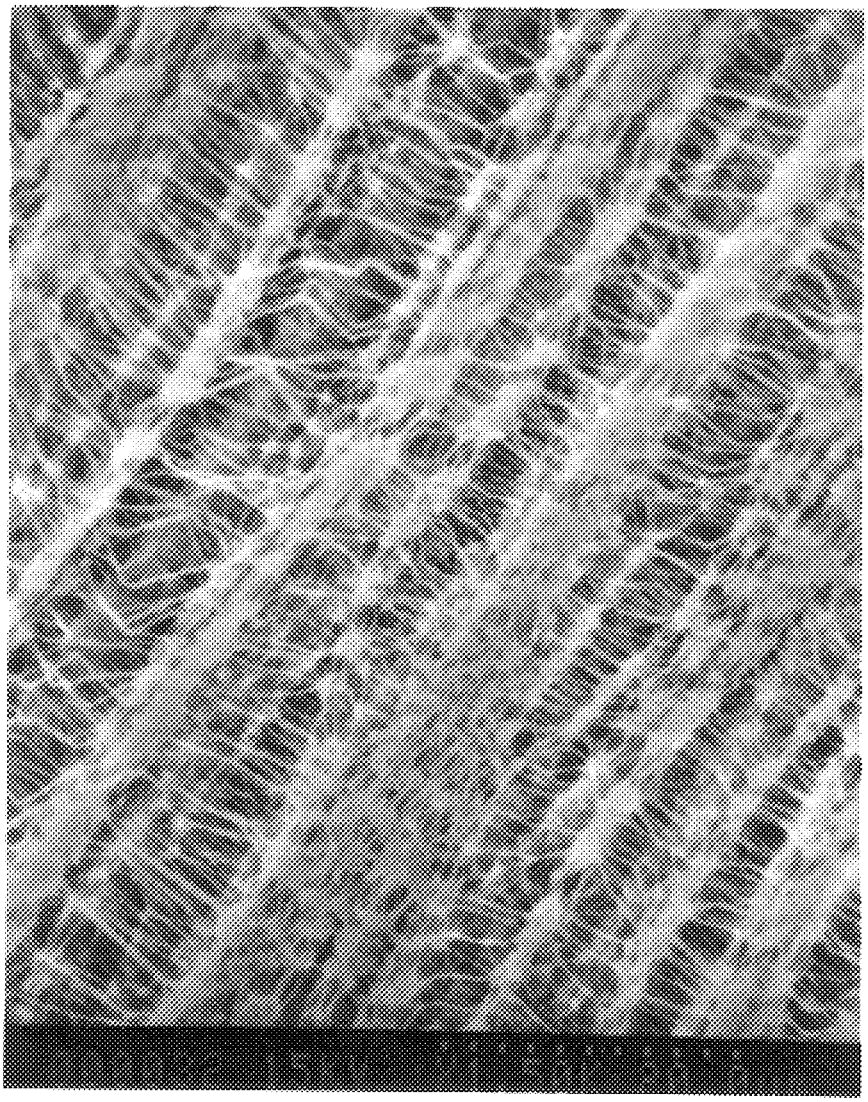
FIG. 6A is a photomicrograph of ePTFE material of the type forming the cover of FIG. 6, which has been transversely expanded.
Figure 6A:
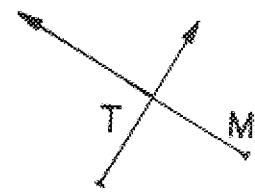
Figure 8:
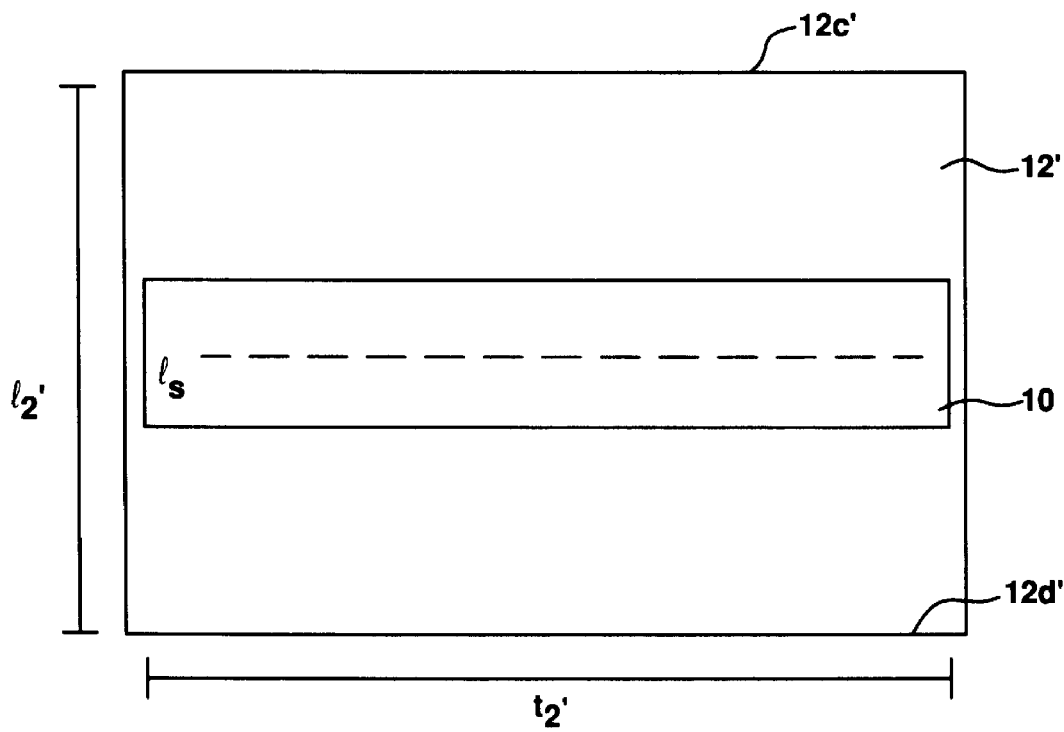
FIG. 8 is a schematic representation of the cover of FIG. 6 applied about the stent.

Referring now to FIG. 6, a further cover 12' which is similar to cover 12 shown in FIG. 3, includes a longitudinal expanse $l_1'$ and a transverse expanse $t_1'$. As mentioned above, given the highly uniaxially oriented nature of the material, cover 12' may be expanded in a transverse direction. In this embodiment of the present invention, cover 12' is transversely expanded prior to placement about stent 10. As shown in FIG. 7, cover 12' is expanded transversely to a transverse dimension of $t_2'$. FIG. 6A shows the structure of the material so expanded where the machine direction is denoted by arrow M and the transverse stretched direction is denoted by arrow T. Such transverse expansion causes a corresponding reduction in the longitudinal expanse of cover 12' to a dimension of $l_2'$ which is less than $l_1'$. Stent 10 is then aligned with cover 12 so that its longitudinal stent axis $l_s$ extends along the transverse dimension $t_2'$ of cover 12 as shown in FIG. 8. Cover 12' is then wrapped about stent 10 so that the transverse edges 12c' and 12d' overlap forming a closed seam 14. The overlapped transverse edges 12c and 12d may be secured in a manner similar to that described above with respect to the previous embodiment of the present invention.

While the highly uniaxially oriented material forming cover 12 exhibits little or no expansion capabilities along the longitudinal axis (machine direction, arrows M, FIGS. 6 and 7), if such material has been previously expanded transversely as described herein, the expanded material will, upon longitudinal stretching, stretch back to its original length. By employing the material as so described, the radial expansion of stent 10 can be controlled.

Figure 9:
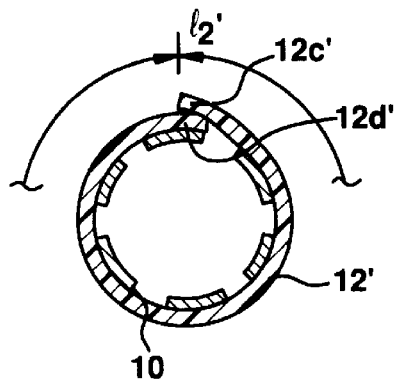
FIG. 9 is a cross-sectional view of the further embodiment of the present invention shown in a compressed state.
Figure 10:
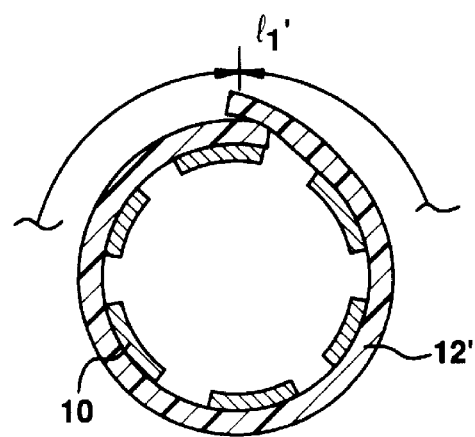
FIG. 10 is a cross-sectional view of the covered stent of FIG. 8 in the radially expanded condition.

As shown in FIG. 9, with the stent 10 positioned with respect to cover 12' as described with respect to FIG. 8, radial expansion of stent 10 from the compressed condition shown in FIG. 9 to the expanded condition shown in FIG. 10 results in a corresponding expansion of the expanded cover 12'. Such expansion occurs along the longitudinal expanse of cover 12'. Since transversely expanded cover 12' is expandable along its longitudinal expanse only to its original length $l_1'$, the radial expansion of stent 12 supported thereunder will therefore be limited. Upon radial expansion of stent 12, the stent will only be expanded to an extent where cover 12' expands to a longitudinal dimension of $l_1'$. Further expansion of stent 10 is limited as cover 12 has reached its maximum expansion capability. By controlling the expansion properties of cover 12 control of the expansion of stent 10 may be achieved.

As cover 12' returns to its original length $l_1'$ upon expansion of stent 10, shortening of its transverse expanse $t_2'$ back to transverse expanse $t_1'$ will occur. This will result in shortening of the cover about the stent 10. Such effects of shortening can be reduced by placing stent 10 with the stent axis $l_s'$ slightly orthogonal with respect to transverse extent $t_2'$. While still providing a limit to the expansion of stent 10, the adverse effects of shortening will be thereby reduced.

Figure 11:
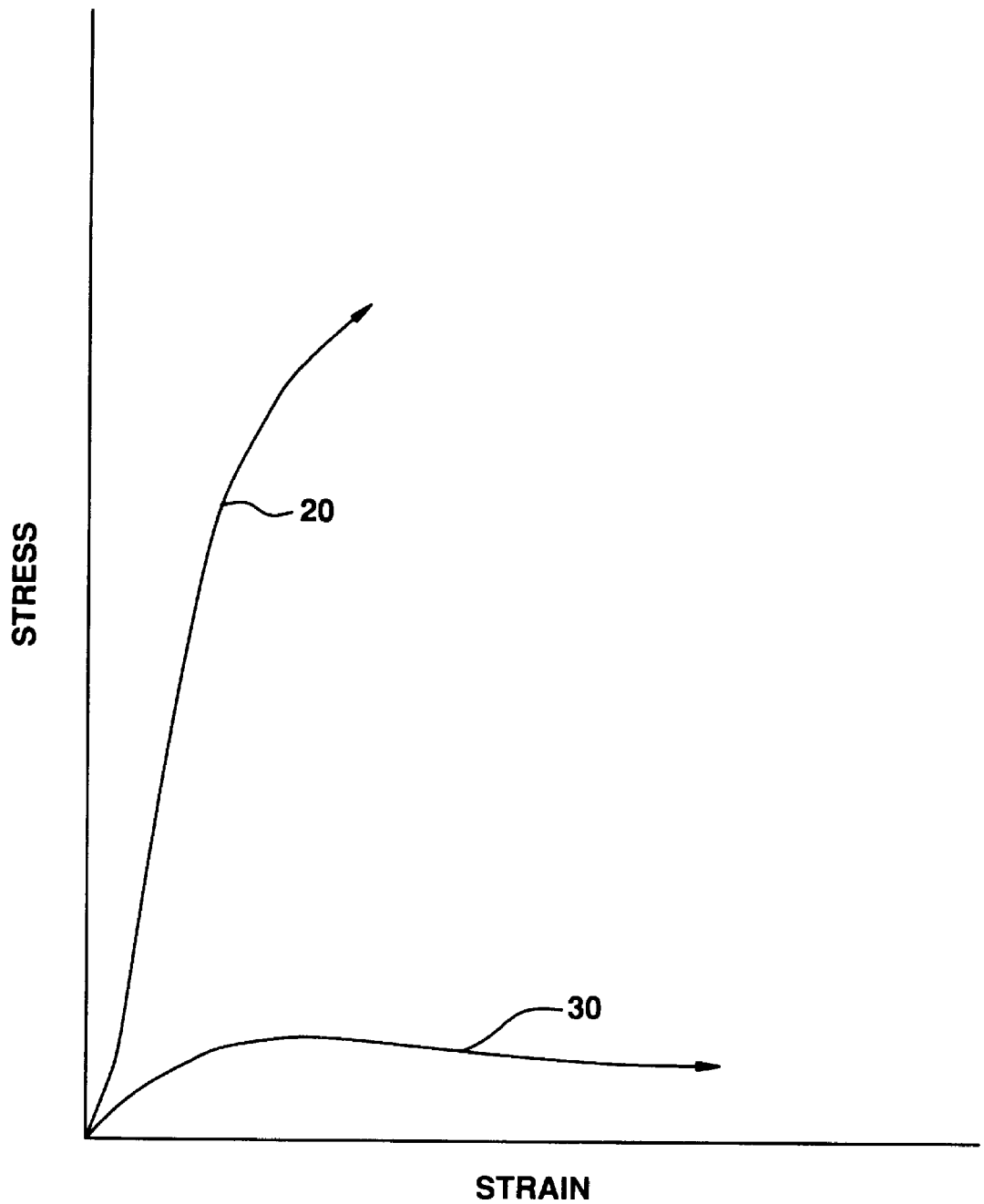
FIG. 11 is a graft illustrating the properties of the material forming the cover of the device of the present invention.

The present invention is described in its preferred embodiment employing ePTFE as the material forming covers 12 and 12'. As ePTFE is highly uniaxially oriented along its machine direction, it exhibits the desirable expansion properties described herein. However, the present invention is not limited to solely ePTFE. Other expandable biocompatible polymer materials, such as polyurethane, which exhibit a high degree of uniaxial orientation in the direction of extrusion of the material may also be employed in combination with the present invention. Such materials are useful in the present invention in that the materials exhibit different stress properties in a direction along the longitudinal axis and in a direction transverse thereto. The characteristics of materials useful in the present invention are shown in the graph of FIG. 11 which is a relative schematic representation, where stress of the material is plotted along the y axis while strain is plotted along the x axis. Curve 20 shows the stress/strain relationship of the material along the machine direction while curve 30 shows the stress/strain characteristics of the material in a direction 90° with respect thereto. Materials exhibiting such properties will be useful in the composite device of the present invention. For example, such other materials may include polyesters such as polyethylene terepthalate (PET), polypropylenes, polyamides, nylons, and copolymers and mixtures thereof, among others.

The present invention farther contemplates incorporating various biological agents in the cover. Agents such as collagen and/or heparin or other drugs or agents may be incorporated into cover 12 for various known therapeutic purposes. Such combinations are shown and described in commonly assigned International Patent Application No. WO 95/29647, published on Nov. 9, 1995 and its priority U.S. applications Ser. No. 235,300 filed Apr. 29, 1994 and Ser. No. 350,233 filed Dec. 6, 1994 which are incorporated by reference herein.

Various changes and modifications can be made to the invention, and it is intended to include all such changes and modifications as come within the scope of the invention as is set forth in the following claims.

What is claimed is:

1. A composite intraluminal device comprising:

an elongate radially expandable tubular stent having an interior luminal surface and an opposed exterior surface extending along a longitudinal stent axis; and a stent cover positioned about the stent and which is formed of unsintered ePTFE which is expandable upon said radial expansion of said stent, wherein said stent covering includes an elongate segment of said unsintered ePTFE having an original longitudinal expanse, said segmnent being expanded in a transverse direction so as to reduce said original longitudinal expanse, said segment being positioned generally transverse to said longitudinal stent axis, and being expandable longitudinally upon said radial expansion of said stent to return said expanded segment to said original longitudinal expanse to thereby control said radial expansion of said stent.

2. A composite intraluminal device of claim 1 wherein said stent is radially expandable from a first compressed state permitting intraluminal delivery to a second expanded state permitting intraluminal deployment.

3. A composite intraluminal device of claim 1 wherein said elongate segment is generally uniaxially oriented along said original longitudinal expanse.

4. A composite intraluminal device of claim 1 wherein said segment is joined about said stent along a seam formed by opposed overlapped transverse ends of said segment.

5. A method of forming an intraluminal device comprising the steps of:

providing an elongate radially expandable tubular stent;

forming a stent cover from a longitudinal segment of unsintered EPTFE having a first longitudinal expanse and a transverse expanse, expanding said segment along said transverse expanse to provide a second transverse expanse greater than said first transverse expanse and a second longitudinal expanse less than said first longitudinal expanse; and applying said expanded segment about said stent, with said second transverse expanse extending longitudinally along said elongate stent.

6. A method in accordance with claim 5 wherein said applying step includes wrapping said cover exteriorly about said stent.

7. A method in accordance with claim 6 wherein said wrapping step further includes:

overlapping opposed longitudinal of said stent cover.

8. A method in accordance with claim 7 further including the step of:

securing said overlapped longitudinal ends of said stent cover together.

9. A method of claim 8 wherein said securing step includes:

adhesively securing said overlapped longitudinal ends.

10. A method in accordance with claim 8 wherein said securing step includes:

compressively securing said overlapped longitudinal ends.

11. A method in accordance with claim 6 wherein said wrapping step includes:

wrapping said expanded segment about said stent with said second longitudinal expanse extending generally transverse to said elongate stent.

12. An intraluminal stent assembly comprising:

a radially expandable stent having a longitudinal stent axis;

a stent cover positioned about said stent and being formed of a generally uniaxially oriented polymer, said stent cover being oriented in a first direction and expanded in a second direction transverse to said first so as to decrease the length of said stent cover from its original length, said longitudinal axis of said stent being aligned with said second direction, so that said stent cover is expandable in said first direction to its original length upon said radial expansion of said stent to control said radial expanse of said stent.

13. A stent assembly of claim 12 wherein said expanded stent cover is expandable in its first direction up to its original length.

14. A stent assembly of claim 13 wherein said uniaxially oriented polymer includes unsintered ePTFE.

* * * * *

UNITED STATES PATENT AND TRADEMARK OFFICE
CERTIFICATE OF CORRECTION

PATENT NO. : 5,824,046
DATED : October 20, 1998
INVENTOR(S) : Smith, et al.

It is certified that error appears in the above-identified patent and that said Letters Patent is hereby corrected as shown below:

Column 8, Line 37      now reads "EPTFE",
should read --ePTFE--.

Column 8, Line 51      now reads "longitudinal",
should read --longitudinal ends--.

Signed and Sealed this

Fourth Day of May, 1999

Q. TODD DICKINSON

Attest:

Attesting Officer      Acting Commissioner of Patents and Trademarks